(12) United States Patent
Mattsson

(10) Patent No.: US 6,209,142 B1
(45) Date of Patent: *Apr. 3, 2001

(54) MALE INCONTINENCE POUCH

(75) Inventor: Lars Mattsson, Hallingsjo (SE)

(73) Assignee: Sorbinco Maskin AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,062

(22) Filed: Apr. 6, 2000

Related U.S. Application Data

(63) Continuation-in-part of application No. 09/331,338, filed as application No. PCT/SE97/02186 on Dec. 19, 1997, now Pat. No. 6,105,174.

(51) Int. Cl.[7] .............................. A41B 9/00; A61F 5/44
(52) U.S. Cl. ................ 2/403; 2/400; 2/403; 604/349; 604/385.1
(58) Field of Search .................. 2/400, 403; 604/385.1, 604/37, 394, 392, 393, 398, 358, 364–349, 304, 308, 317, 327, 355, 350–353; 602/67–73, 79, 58, 41

(56) References Cited

U.S. PATENT DOCUMENTS

| | | | |
|---|---|---|---|
| 2,933,085 | * | 4/1960 | Jacques ................................. 602/67 |
| 3,570,491 | * | 3/1971 | Sneider ............................. 604/385.2 |
| 4,182,334 | * | 1/1980 | Johnson ............................ 604/385.2 |
| 4,197,849 | * | 4/1980 | Bostick ................................ 604/318 |
| 4,200,103 | * | 4/1980 | Black et al. ......................... 604/366 |
| 4,453,938 | * | 6/1984 | Brendling ............................. 604/346 |
| 4,590,931 | * | 5/1986 | Kidwell, Jr. ........................... 602/70 |
| 4,627,846 | * | 12/1986 | Ternstrom ............................ 604/349 |
| 4,710,188 | * | 12/1987 | Ryneman .......................... 604/385.1 |
| 4,731,063 | * | 3/1988 | Newkirk ............................... 604/347 |
| 5,716,350 | * | 2/1998 | Ryan ................................ 604/385.1 |
| 5,935,091 | * | 8/1999 | Friedman ............................... 602/79 |
| 6,105,174 | * | 8/2000 | Nygren et al. .......................... 2/403 |

FOREIGN PATENT DOCUMENTS

WO 9107156   5/1991 (WO).

* cited by examiner

*Primary Examiner*—Gloria M. Hale
(74) *Attorney, Agent, or Firm*—Fasth Law Offices; Rolf Fasth

(57) ABSTRACT

The male incontinence pouch allows the user to sealingly insert the penis through an openable opening into a cavity defined in the pouch device. The incontinence pouch has an outer liquid-proof polyethylene layer. A soft fibrous nonwoven material is attached to the polyethylene layer. An inner liquid-permeable material is applied to the nonwoven material. An absorption layer is disposed between the polyethylene layer and the liquid-permeable material to form a laminate. An edge portion of the liquid-permeable material is attached to another edge portion of the liquid-permeable material so that the cavity is formed therebetween at an upper side surface of the incontinence pouch. The laminate in folded inwardly along a cross-folding line so that a side wall is formed.

15 Claims, 6 Drawing Sheets

MALE INCONTINENCE POUCH

PRIOR APPLICATION

This is a continuation-in-part application of U.S. patent application Ser. No. 09/331,338 filed Jun. 15, 1999, now U.S. Pat. No. 6,105,174 which is a 371 of PCT/SE97/02186 filed Dec. 19, 1997.

TECHNICAL FIELD

The present invention relates to a male incontinence pouch that is adapted to absorb urine.

BACKGROUND AND SUMMARY OF THE INVENTION

The purpose of the present invention is the eliminate the known drawback that impair existing incontinence pouches. In an incontinence pouch known from Swedish patent SE-8303663-2 there is as patent criterion a recess around the scrotum in order to accommodate both penis and scrotum. In other words, one has optimized the incontinence pouch for men with what i: termed a retracted penis, And in another incontinence pouch, known from Swedish patent SE-8400056-1, it is stated with regard in its male version that the incontinence pouch in characterized by being used for the opposite purpose, namely solely for penile application. It is also so with the other incontinence pouches commercially available on the market. This is also confirmed by the fact that there in today no form of incontinence pouch that basically functions well for these two means of application.

Swedish patent SE-8303963-2 discloses an incontinence pouch with a recess defined therein that implies that men with what is termed a normal penis can more easily slide out of the recess in the incontinence pouch and that overfilling definitely occurs more easily with this relatively deep recess, especially when men are in a sitting posture.

Swedish patent SE-8400056-1 seems; to exclude men with a retracted penis for scrotal application an it in too narrow, for which reason this incontinence pouch is now sold for normal penile applications solely. Should the pouch be used fox men with a retracted penis, the penis will easily slide out, whereby the small available overlapping absorbent surface in the incontinence pouch will imply a major risk of leakage. Under the existing patent criteria there is no means of generating a functioning pouch intend to enclose both penis and scrotum.

One object of the male incontinence pouch of the present invention is to solve the above described problem.

The present invention is a male incontinence pouch that allows the user to insert the penis through an opening into a cavity defined in the pouch device. The incontinence pouch has an outer liquid-proof polyethylene layer. A soft fibrous nonwoven material is attached to the polyethylene layer. An inner liquid-permeable material is applied to the nonwoven material. An absorption layer in disposed between the polyethylene layer and the liquid-permeable material to form a laminate. An edge portion of the liquid-permeable material is attached to another edge portion of the liquid-permeable material so that the cavity is formed therebetween at an upper side surface of the incontinence pouch. The laminate is cross-folded inwardly so that a side wall is formed.

DETAILED DESCRIPTION

Figure 2:
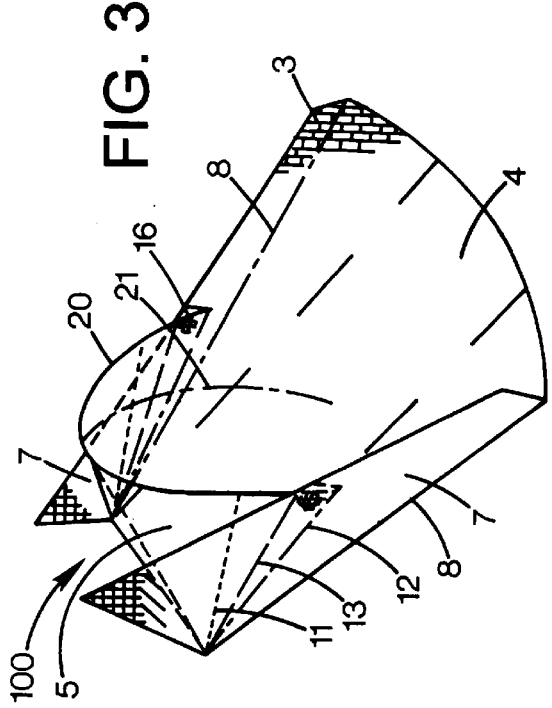
FIG. 2 is a perspective view of the male incontinence pouch device of the present invention in a partially folded position.
Figure 3:
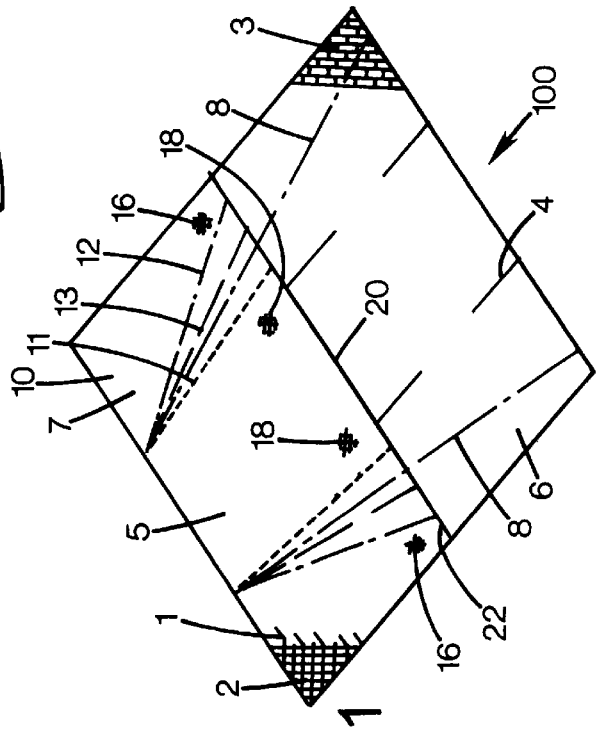
FIG. 3 is a perspective view of the male incontinence pouch device of the present invention in an expanded position.
Figure 1:
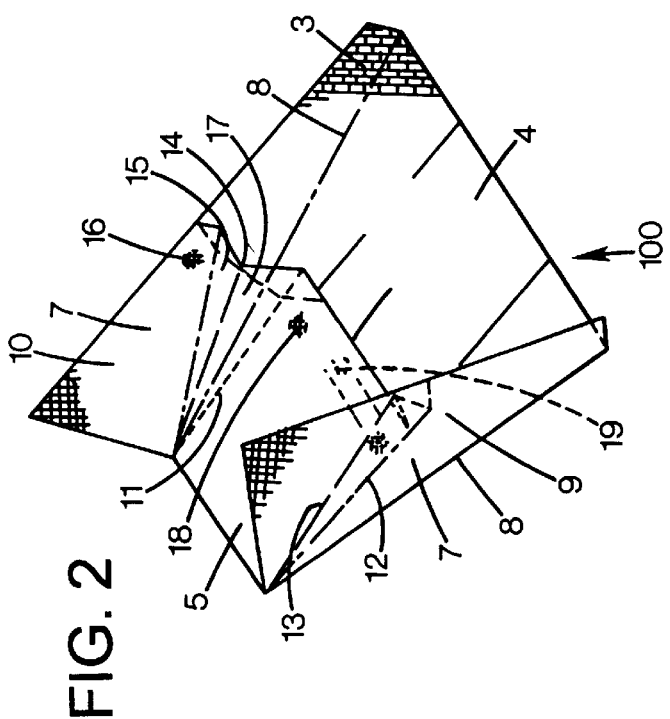
FIG. 1 is a perspective view of the male incontinence path device of the present invention in a flat position.

The male incontinence pouch 100, shown in FIGS. 1–3, comprises an outer liquid-proof layer 1, such as a polyethylene film layer that may be provided with a soft fibrous material 2, such an a nonwoven material, on its exterior surface. The material 2 may be used to avoid having the polyethylene film layer to be applied directly against the male body. The incontinence pouch also has an inner liquid-permeable material 3. The pouch also has an absorption layer 4 that is applied directly between the liquid-proof layer 1 and the liquid-permeable material 3 so as to form a bag shape by folding and sealing the material 3 against another portion of the material 3. The area where the material 3 is folded and sealed against the same material 3 forms an upper side surface 5 intended to face the male body and that is 40–60% shorter than the under side surface 6 that is intended to be placed against underwear or the like.

A side portion 7 in delineated by a cross-folding line 8 and may be folded inwardly towards the upper aided surface 5. An outside 9 and an inside 10 of the side portion 7 are thus formed and both sides have an equal length. However, a pleat 14 may be obtained by double-folding the inside 10 outwardly along an inner base line 11 and outer base line 12 with a top fold line 13 located between them. The pleat 14 has an upper side 15 that is attached to the opposite inside 10 with a permanent adhesive 16. An underside 17 of the pleat 14 is removably attached to the upper side surface 5 by an adhesive 18. An alternative to the adhesive 18 is a separatable ribbon 19 or the like that may be attached to the outside 9 and extend across the sides 7. Adhesive in this context may refer to a variety of sealing material such as glue, cold-glue, hot-melt, lacquer, wax, VELCRO loop fasteners, zip ribbons, etc. It is to be understood that the removable adhesive 18 may not be applied at all so that the pouch is then primarily adapted for men with a retracted penis where the fold itself may be unfolded during application. The removable adhesive 18 may be replaced by a permanent adhesive 16 so that the pouch is primarily adapted for men with a normal penis.

When using the incontinence pouch for a normal penis, the incontinence pouch may be used without separating the removable adhesive 18 or the separatable ribbon 19. An upper edge 20 of the upper side surface 5 may be raised to an optimal highest position when the removable adhesive 11 or the separable ribbon 19 has been separated The angle of the outer base line 12 relative to the pleat 14 determines the length of the upper edge 20 and the pull-down angle 21. Also, the position of the outer base line 12 on the upper edge 20 in relation to where the side-edge meal in located, affects the length of the upper edge 20. That is, if the location of the outer base line 12 on the upper edge 20 is below the side-edge seal, the distance between them may produce an increase of the width of the available upper edge 20. It thus follows that if this distance is in any way sealed, this increase may be eliminated. This alternative may be desirable if the permanent adhesive 19 has net been applied and it is possible to obtain a determination of the width of the upper edge 20 without having to fold the pleat 14 inwardly. This alternative is also desirable if the adhesive 16 is replaced with the removable adhesive 18 which also, in this case, produces a 2-step product that is both adapted for normal penile and penile-scrotal applications. A relative drawback is that when the upper side surface 5 is not attached to the inside 10, an opening can be obtaining there during use.

In practice, the present invention may, in one and the same product, be optimized for a penis only or the combination of a penis and scrotum. This is partly due to the upper edge 20 of the upper side surface 5 that in like a cylindrical container and may be applied at the root of the penis when used for a penis only. When applied to the combination of a penis and scrotum, the upper edge 20 may be removed and pulled down and adapted in an anatomically correct manner so that the upper edge 20 is a downwardly hanging and somewhat outwardly angled U-shape.

Underwear tape may be used to securely attach the incontinence pouch to underpants, sanitary briefs or the like.

With reference to FIGS. 4–8, an alternative embodiment of the male incontinence pouch device 200 of the present invention is shown. The pouch device 200 has an outer liquid-proof layer 202, such as a polyethylene film layer, that may have a soft fibrous material 204, such as a nonwoven material, on an exterior surface of the layer 202. The material 204 may be used to avoid having the polyethylene film layer to be applied directly against the skin of the person wearing the pouch device 200. Preferably, the pouch device 200 also has an absorption layer 206 that is positioned directly between the liquid-proof layer 202 and a liquid-permeable material 208. The absorption layer 206 is adapted to absorb large quantities of liquid ouch as urine. In this way, the layer 202, the material 204, the layer 206 and the material 208 may form a laminate structure 210. The laminate structure 210 may be folded along a folding line 212 to form a bag shape when the material 208 of a under section 21A faces the material 20A of a upper section 216 and the under section 218 and the upper section 216 are sealed along an edge sealing section 217. The under section 218 may face the skin of the person wearing the pouch device 200 while the upper section 216 may be placed inside or adhered to underwear or the like worn by the person.

A first corner portion 220 may be folded upwardly along a folding line 222 towards the upper section 216 to make an end portion 224 of the pouch 200 more narrow so that it batter fits inside the underwear of the person. Similarly, a second corner portion 226 may be folded upwardly along a folding line 228 towards the upper section 216. Both portions 220 and 226 my be attached to an upper side 215 of the upper section 216. For example, an adhesive 225 may be used to adhere an inside of the portions 220, 226 to the upper side 215 of the upper section 216.

Figure 4:
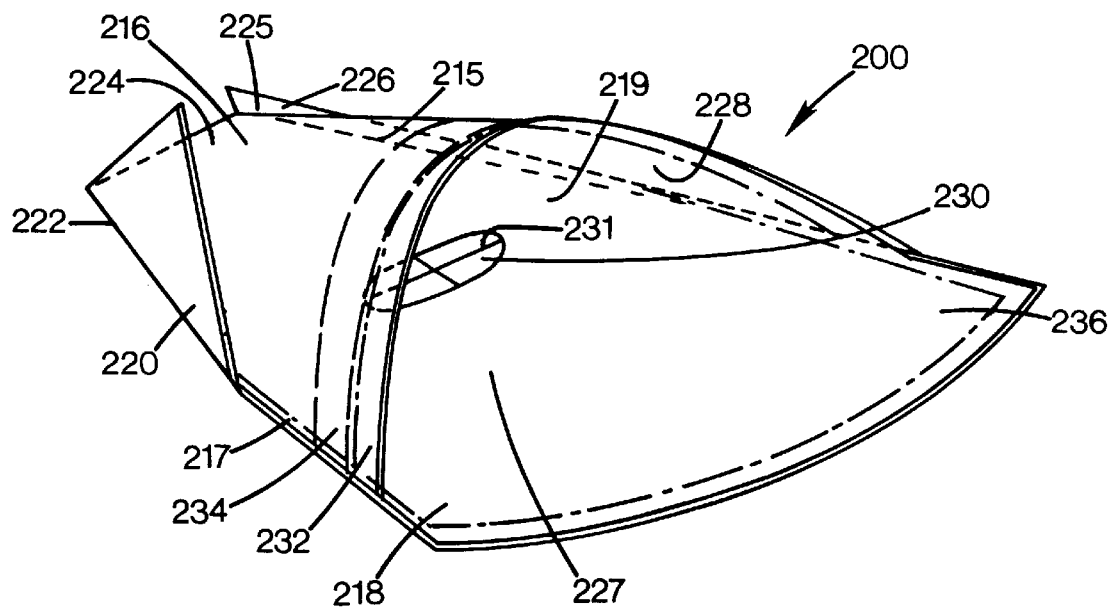
FIG. 4 is a perspective view of an alternative embodiment of the male incontinence pouch device of the present invention in an expanded position.
Figure 5:
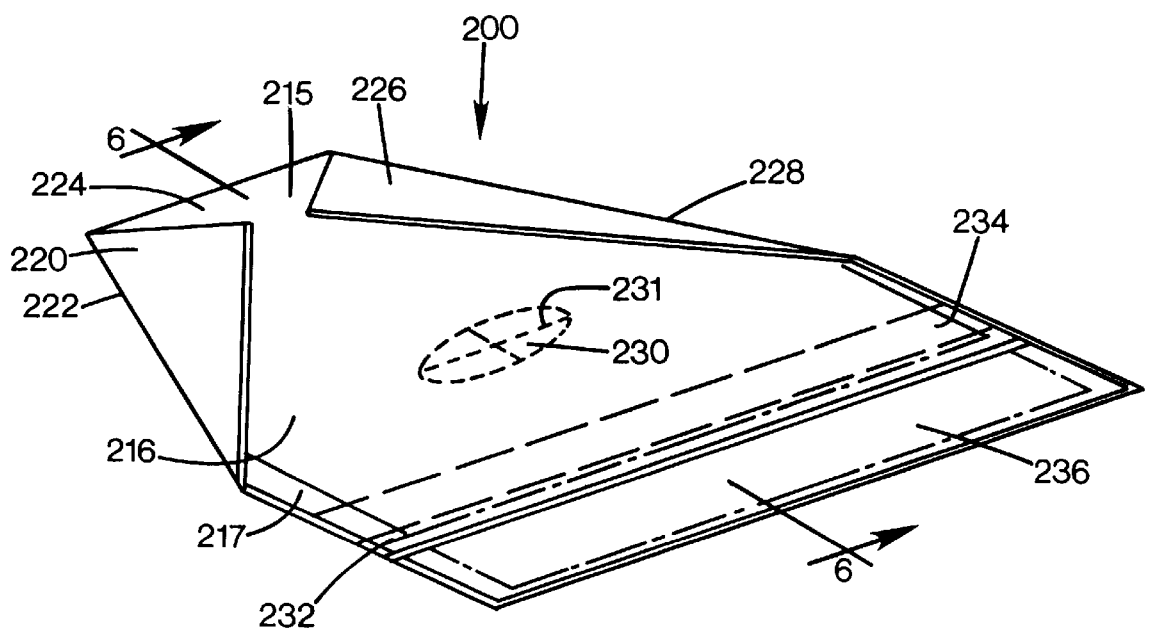
FIG. 5 is a perspective view of the embodiment of FIG. 4 is a flat position.
Figure 6:
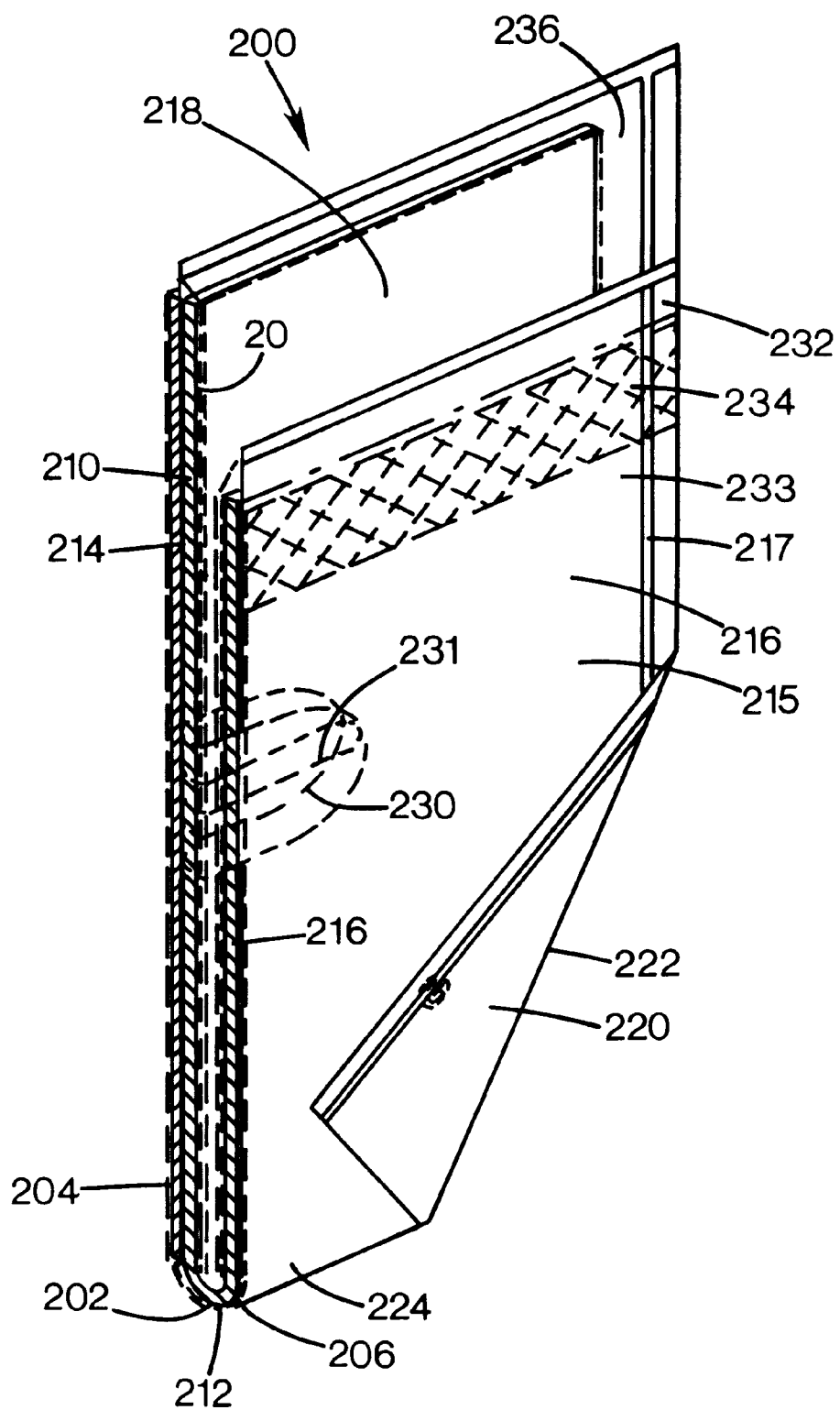
FIG. 6 is a cross-sectional perspective view along the line 6—6 in FIG. 5.

As best shown in FIG. 4 and as indicated above, an important feature of the present invention is that the upper section 216 may be lifted or separated from the under section 216 so that a cavity or pouch 219 may be formed therebetween that is closed at the end portion 224. In this way, the soft material 208 may constitute a bottom 227 of the pouch 219 and the material 208 is also inside wall 228 of the upper section 216 when the upper section 216 is separated from the under section 218.

The bottom 227 has an opening 230 defined therein that is adapted to receive a penis. The opening 230 should fit around the penis to prevent leakage. The opening 230 may be round, oval or any other suitable shape. For example, the opening 230 may have a member 221 that may be adapted to fit around the root portion of the penis to prevent urine from leaking out through the opening 230. The member 231 may be heat-sealed with a thinner weakness disposed In the middle thereof or combined thin and perforated weakness member that may be separated as needed to fit the root portion of the penis. Large root portions may require more of the member 231 to be separated or opened. In the alternative, the member may be an additional resilient member that is integratedly sealed with the liquid-permeable material 208, the outer liquid-proof layer 202 and the soft fibrous material 204. In the preferred embodiment, the part of the opening 230 that extends through the absorption layer 206 should have a size that is slightly larger than the size of the portion of the opening 230 that extends through the other segments of the laminate 210. In other words, the layer 206 may define an absorption opening that is greater than the openings defined by the layer 202, the material 204 and the material 208. However, the various openings are aligned to together form the opening 230. The reason for the larger absorption opening in that the layer 206 absorbs urine and should not be in direct contact with the penis. Some users may even be allergic to a long term contact with the layer 206 soaked with urine. The pouch 219 provides access to enable the person to pull the penis, that has been partially inserted, through the opening 230, if necessary, and place the penis in a proper position inside the pouch 219 so that the penis may face the bottom 224.

An upper portion 233 of the upper section 216 may have an adhesive section 234 applied thereto. The section 234 may be any adhering surface, including, but not limited to, a variety of sealing material such as glue, cold-glue, hot-melt, lacquer, wax, VELCRO loop fasteners and zip ribbons.

When the entire penis in properly inserted through the opening 230, an excess segment 236 of the under section 218 that extends beyond the upper section 216 may be around the edge segment 232 of the absorption layer 206 over the adhesive section 234 to close the pouch 219 by removably attaching the segment 236 on the adhesive section 234. This attachment may be leak proof. When it is time to change the pouch device 200, the user simply pulls the penis out of the opening 230 and dispose of the pouch device 200. It is not necessary to open the pouch 219 again to remove the pouch device 200 from the penis. In the alternative, the excess segment 236 may have an outer edge that is attached to an outer edge of the upper section 216.

Figure 7:
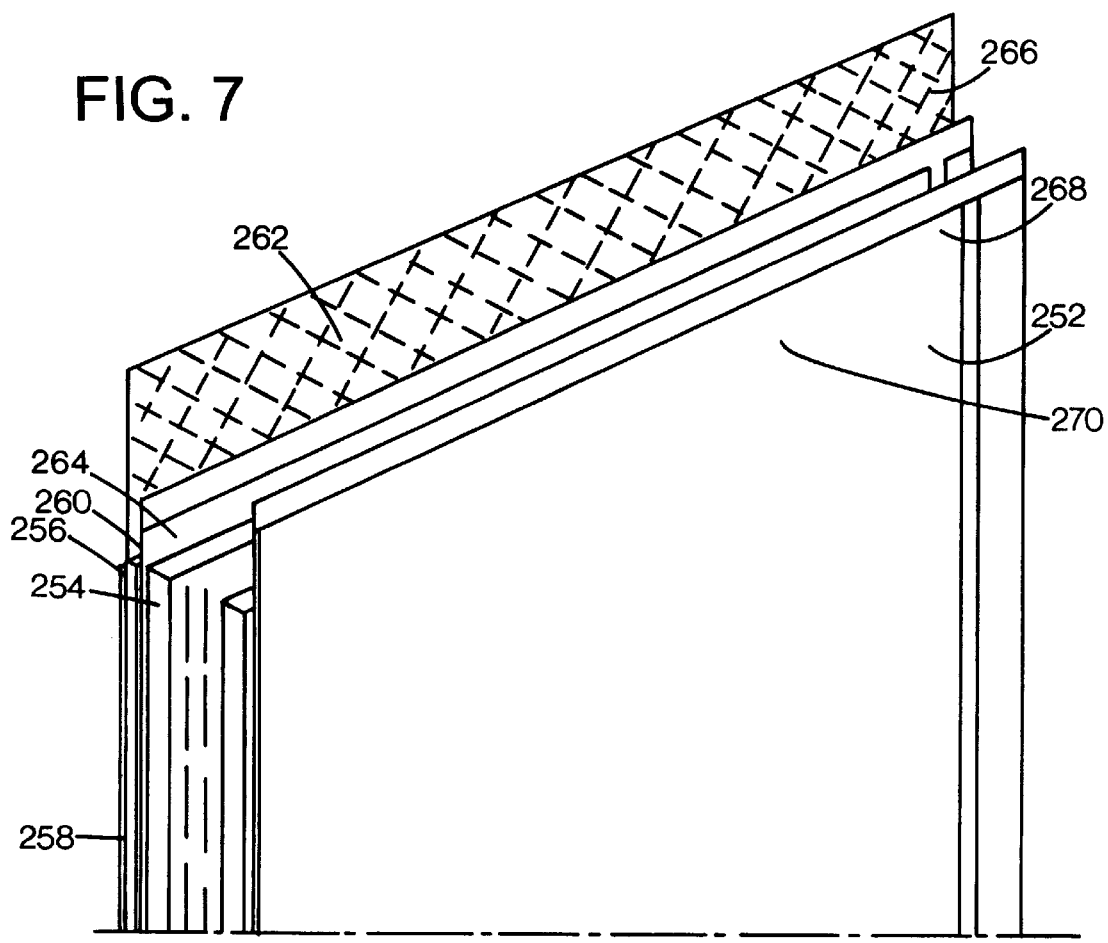
FIG. 7 is a detailed perspective view of a second embodiment of the male continence pouch device of the present invention.
Figure 8:
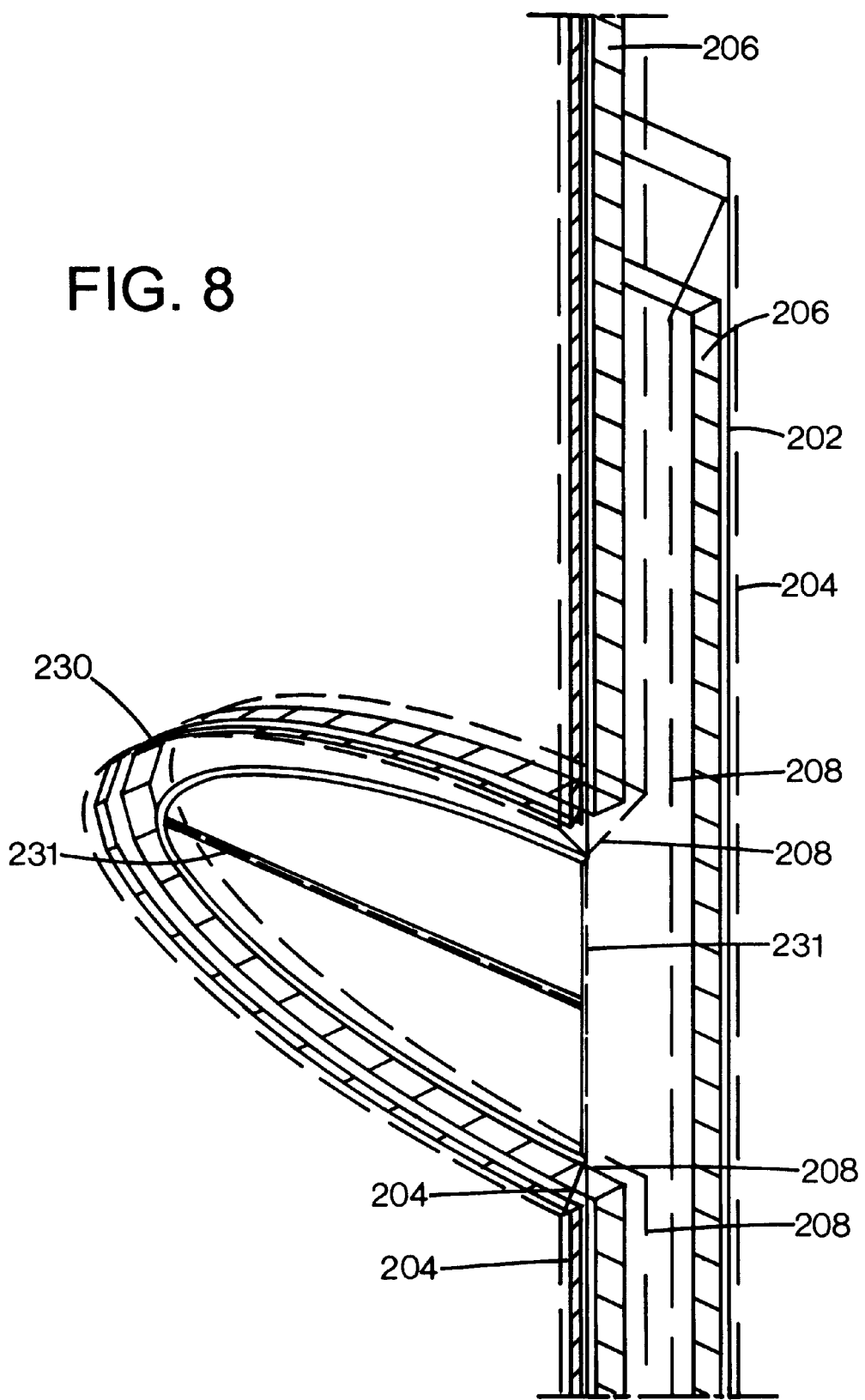
FIG. 8 is a detailed perspective view of the opening the male incontinence pouch of the present invention.

FIG. 7 shows an alternative embodiment of a male pouch device 250 the present invention. The device 250 has an upper aide 252 that has a length that is equal to or substantially equal to a length of an under side 254. The device 250 is identical to the device 200 except to the differences described herein. The devices may also consist of an additional layer 256 that is placed between a soft fibrous material 258 and an outer liquid proof layer 260. The additional absorbent layer 256 also ham an opening similar or identical to the opening 230 described above so that the penis may be inserted through all the various layers. The layer 256 may absorb any urine or other substances that may leak back out through the opening.

An adhesive section 262 may be placed on top of the is under side 254 on the soft fibrous material 258 or, if so desired, on the outer liquid proof layer 260. In this embodiment, the upper section 252 and the under section 254 may be equal in size and the adhesive section 262 may protrude beyond an edge segment 264 of the under section 254 so that an excess segment 266 is formed by the adhesive section 262. The excess segment 266 may be folded around the edge segment 264 and an edge segment 268 and be attached at an upper portion 270 of the upper section 252. Preferably, this attachment is leak proof. The adhesive section may also be disposed between the upper section 252 and the under section 254 by a double adhesive tape or any other closable mechanism such as zip lock and VELCRO hook and loop fasteners.

Figure 9:
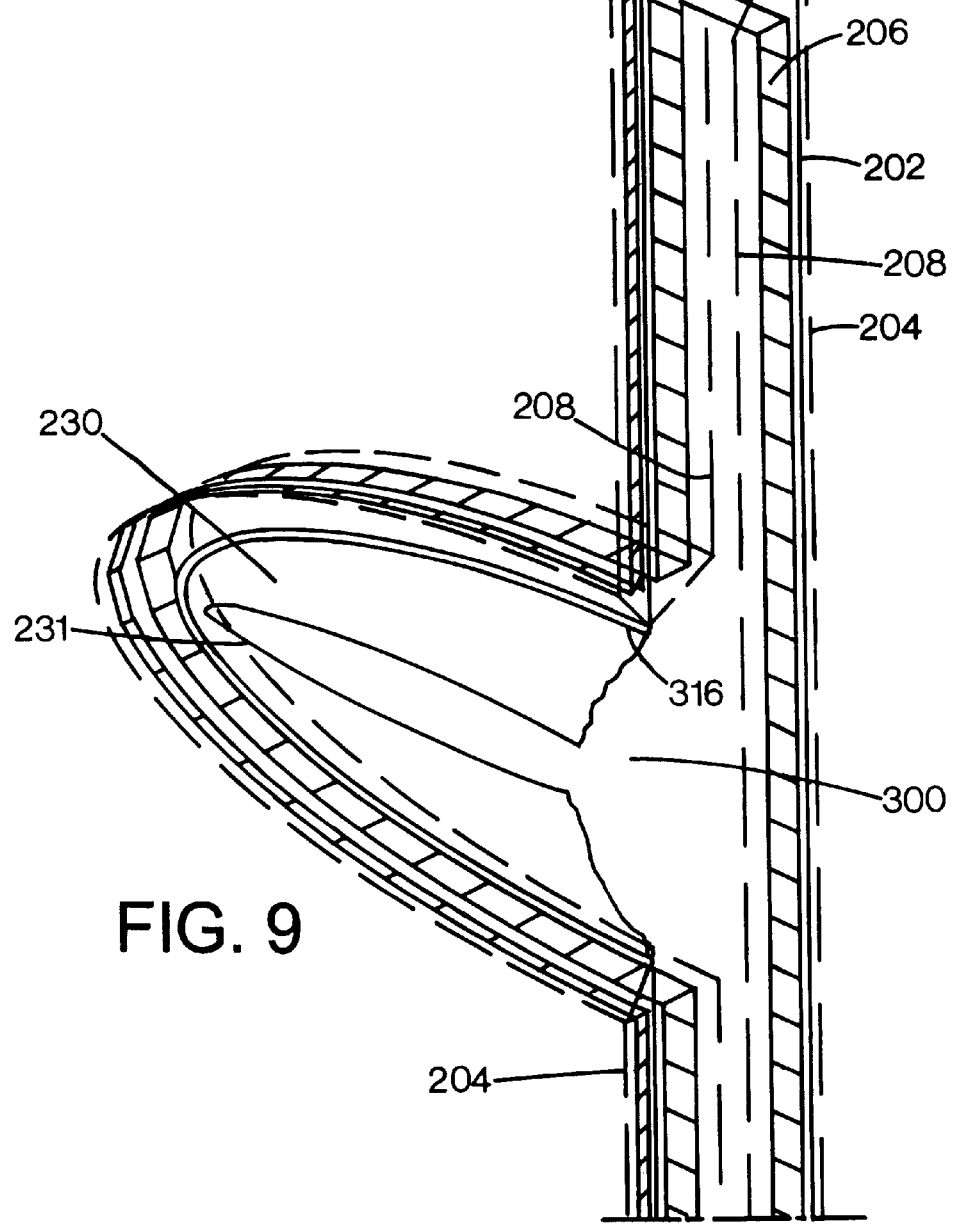
FIG. 9 is a detailed perspective view of the opening of an alternative embodiment of the male incontinence pouch device the present invention.

FIG. 9 Shows an alternative membrane mechanism 300 in the opening 230. The liquid-permeable material 208, the outer liquid-proof layer 202 and the soft fibrous material 204 are, preferably, adhered to one another or heat-sealed together to create an outer edge 315. A resilient member 302 may be disposed inside the opening and be sealingly integrated with the outer edge 316. The member 302 may sealingly fit around the penis so that larger penises will extend the member 302 closer to the edge of the opening 230.

Figure 10:
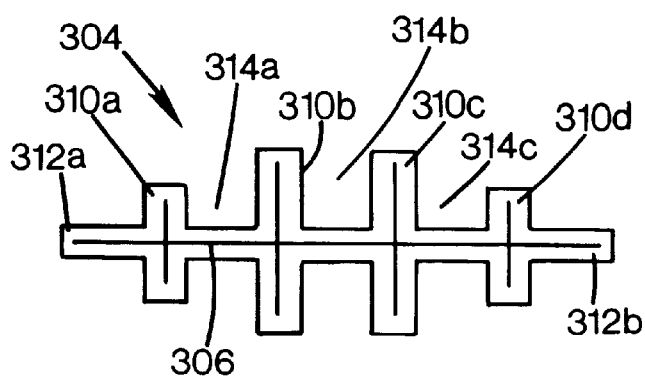
FIG. 10 is a cross-sectional view of a portion of a membrane covering the opening of the male incontinence pouch device of the present invention.

FIG. 10 shows a portion of a membrane 304 that has a plurality of perforated weakness members 306 that are both horizontally and vertically directed. Similar to the membrane 300, the membrane 304 consists of the liquid-permeable material, the outer liquid-proof layer and the soft fibrous material that are adhered to one another to form the membrane. More particularly, the membrane 304 ham vertical protrusion segments 310a, 310b, 310c, 310d and horizontal protrusion segments 312a and 312b. Laminate sections 314a, 314b, 314c are disposed between the protrusion segments 310. Similar to the member 231, the members 306 my be separated, as needed, to adjust the size of the effective opening to the size of the penis.

While the present invention has been described in accordance with preferred compositions a embodiments, it is to be understood that certain substitutions and alterations may be made thereto without departing from the spirit and scope of the following claims.

I claim:

1. A male incontinence pouch comprising:
   an outer liquid-proof layer having an exterior surface;
   an absorption layer applied to the liquid-proof layer;
   an inner liquid-permeable material applied to the absorption layer to form a laminate therewith;
   a first edge portion of the liquid-permeable material being attached to a second edge portion of the liquid-permeable material so that a cavity is formed therebetween at an upper edge of an upper side portion of the male incontinence pouch;
   an opening defined by the laminate that is in fluid communication with the cavity;
   the laminate being folded inwardly along a cross-folding line so that a side wall is formed; and
   the upper edge being movable between a closed position to close the cavity and an opened position to open the cavity.

2. The male incontinence pouch according to claim 1 wherein the opening is defined by adjustable segments of the liquid-proof layer, a soft fibrous material and the liquid-permeable material.

3. The male incontinence pouch according to claim 1 wherein a soft fibrous material is applied to the exterior surface of the outer liquid-proof layer, the soft fibrous material has an adhesive segment applied thereto.

4. The male incontinence pouch according to claim 3 wherein a portion of the liquid-permeable material is attached to the adhesive segment to close the cavity.

5. The male incontinence pouch according to claim 1 wherein a membrane extends across the opening.

6. The male incontinence pouch according to claim 5 wherein the membrane has a set of perforated weakness members so that a size of an effective opening is adjustable by separating the weakness members.

7. The male incontinence pouch according to claim 5 wherein an open resilient member is attached to the membrane.

8. The male incontinence pouch according to claim 1 wherein the liquid-permeable material has an adhesive segment applied thereto.

9. A male incontinence pouch comprising:
   an outer liquid-proof polyethylene layer having an exterior surface;
   a soft fibrous nonwoven material applied to the exterior surface;
   an absorption layer applied to the liquid-proof layer;
   an inner liquid-permeable material applied to the absorption layer to form a laminate therewith;
   a first edge portion of the liquid-permeable material being attached to a second edge portion of the liquid-permeable material so that a cavity is formed therebetween at an upper edge of an upper side surface of the incontinence pouch, the upper edge being movable between a closed position and an opened position;
   the laminate being folded inwardly along a cross-folding line no that a side wall in formed, the laminate having an adhesive segment adjacent to the upper edge; and
   an end section extending beyond the upper edge, the end section being foldable over the upper edge and attachable to the adhesive segment to close the cavity.

10. The male incontinence pouch according to claim 9 wherein the laminate has an opening defined therein so that the opening is in fluid communication with the cavity.

11. The male incontinence pouch according to claim 10 wherein a resilient member of the laminate has an opening defined therein.

12. The male incontinence pouch according to claim 10 wherein the pouch has an under side surface that is substantially similar to the upper side surface and is facing a direction that is opposite a direction of the upper aide surface.

13. A method of using a male incontinence pouch on a male with a penis, comprising:
   providing a male incontinence pouch having an outer liquid-proof layer, an absorption layer applied to the liquid-proof layer, an inner liquid-permeable material applied to the absorption layer to form a laminate therewith, a first edge portion of the liquid-permeable material of an upper side segment being attached to a second edge portion of the liquid-permeable material of an under side segment so that a cavity is foxed therebetween, an opening defined by the laminate that is in fluid communication with the cavity;
   separating the upper side segment from the under side segment and providing access into the cavity;
   inserting a portion of an entire penis through the opening;
   pulling the entire penis through the opening; and
   sealing the upper side segment against the under side segment.

14. The method according to claim 13 wherein the method further comprises applying a sealing pressure around the penis.

15. The method according to claim 13 wherein the step of sealing comprises adhering an adhesive segment of the under side segment to the upper side segment.

* * * * *